US008290791B2

(12) United States Patent
Patel et al.

(10) Patent No.: US 8,290,791 B2
(45) Date of Patent: Oct. 16, 2012

(54) PATIENT MANAGEMENT SYSTEM

(75) Inventors: Amisha S. Patel, Maple Grove, MN (US); Luc Roland Mongeon, Minneapolis, MN (US); Susan Heilman Kilbane, Deephaven, MN (US); James E. Willenbring, Saint Paul, MN (US); Christopher John Gennaro, Newton, PA (US)

(73) Assignee: Medtronic, Inc., Minneapolis, MN (US)

( * ) Notice: Subject to any disclaimer, the term of this patent is extended or adjusted under 35 U.S.C. 154(b) by 495 days.

(21) Appl. No.: 12/181,429

(22) Filed: Jul. 29, 2008

(65) Prior Publication Data

US 2010/0030575 A1 Feb. 4, 2010

(51) Int. Cl.
*G06Q 50/00* (2012.01)

(52) U.S. Cl. .................................. 705/3; 705/2

(58) Field of Classification Search .................. 705/2–4; 600/300; 607/30
See application file for complete search history.

(56) References Cited

U.S. PATENT DOCUMENTS

| | | | |
|---|---|---|---|
| 4,987,897 A * | 1/1991 | Funke ............................. | 607/32 |
| 5,720,771 A | 2/1998 | Snell | |
| 6,272,379 B1 | 8/2001 | Fischell et al. | |
| 6,418,346 B1 | 7/2002 | Nelson et al. | |
| 6,442,432 B2 | 8/2002 | Lee | |
| 6,480,745 B2 * | 11/2002 | Nelson et al. .................. | 607/60 |
| 6,766,327 B2 | 7/2004 | Morgan et al. | |
| 6,920,360 B2 * | 7/2005 | Lee et al. ......................... | 607/60 |
| 6,937,150 B2 | 8/2005 | Medema et al. | |
| 7,265,676 B2 | 9/2007 | Gordon et al. | |
| 7,289,851 B2 | 10/2007 | Gunderson et al. | |
| 2006/0017575 A1 | 1/2006 | McAdams | |
| 2006/0122864 A1 | 6/2006 | Gottesman et al. | |
| 2006/0247709 A1 | 11/2006 | Gottesman et al. | |
| 2007/0060797 A1 * | 3/2007 | Ball et al. ...................... | 600/300 |
| 2007/0167986 A1 | 7/2007 | Gunderson | |
| 2007/0179567 A1 | 8/2007 | Gennaro | |
| 2008/0021741 A1 * | 1/2008 | Holla et al. ....................... | 705/3 |

OTHER PUBLICATIONS

International Search Report, PCT/US2009/051228, 4 pages.

* cited by examiner

*Primary Examiner* — Michelle Le

(57) ABSTRACT

Embodiments of the present invention provide a system in which a medical device selects less than all of its stored information and provides the selected subset of information to a data mart for storage, processing, and/or communication to one or more interested parties. In many embodiments, customers, patients, or even components of the medical device or of the remote patient management system can access selected medical device information (e.g., customers can access medical device information tailored to the care they are providing to one or more patients). In many embodiments, customers can receive such medical device information according to a schedule that best suits their care (or whenever they desire such information, irrespective of a schedule). In many embodiments, providing less than full transmissions to the data mart reduces the strain on medical device batteries.

30 Claims, 4 Drawing Sheets

PATIENT MANAGEMENT SYSTEM

BACKGROUND

Some embodiments disclosed herein relate to patient management systems and, more particularly, to patient management systems for controlling the type and/or quantity of information communicated between a medical device, a data mart, one or more customers, and/or the patient.

Medical devices are being offered with increasing capacity for storing physiological and device performance data. Moreover, the use of home monitoring instrumentation and equipment is gaining popularity for managing patients with chronic illnesses. Physiological sensors for monitoring various patient conditions may operate in connection with a medical device and home based instrumentation for acquiring continuous or periodic physiological data for processing and/or storage by the medical device or for clinical management. Such data may be used by the medical device in automated therapy delivery or by a clinician in diagnosing or monitoring a patient condition and in his or her therapy management.

A data mart is a convenient place for storing physiological and device performance data from multiple medical devices. Some data marts can store data from tens of thousands of medical devices. Medical devices typically provide all of the information stored in their memory to the data mart on a periodic basis (e.g., every 90 days). Upon receipt of a full transmission from a medical device, the data mart usually provides all of that information to one or more customers (e.g., physicians, nurses, technicians, physician's assistants, etc.) charged with caring for the patient having the medical device.

Providing such a large volume of information to customer(s) for each patient can pose challenges. In some instances, medical devices collect upwards of 4000 parameters related to patient physiology and device performance. Customers often spend significant amounts of time and energy sorting through the information to get what they need to care for the patient. They could otherwise be spending this time and energy providing enhanced care for their patients. Moreover, full transmissions can put significant strain on medical device batteries.

In many cases, different customers may desire different information at different intervals in caring for the same patient. For example, an electrophysiologist is generally interested in reviewing certain information related to a pacemaker or ICD patient once every three to six months, as long as the patient is not experiencing adverse symptoms. Customers other than electrophysiologists are often interested in reviewing different information related to the same pacemaker or ICD patients at different intervals. For example, a heart failure specialist may desire different information on a more frequent basis. A heart failure specialist is often interested in looking at the clinical trends in the device diagnostics in order to better manage the heart failure. The frequency of data review depends on the condition of the patient. Immediately after a decompensation (heart failure episode where lungs get fluid accumulation), the physician may want to review the device diagnostic data on a daily basis for 1 or 2 weeks after the event but once the patient has stabilized may want to only review these data once a month or once a quarter.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is illustrative in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Embodiments of the present invention provide a system in which the medical device selects less than all of its stored information and provides the selected subset of information to a data mart for storage, processing, and/or communication to one or more interested parties. In some embodiments, such systems include various equipment, as discussed elsewhere herein, performing methods for remotely caring for patients having medical devices. In many embodiments, each interrogation can trigger the transmission of only a tailored set of information.

Figure 1:
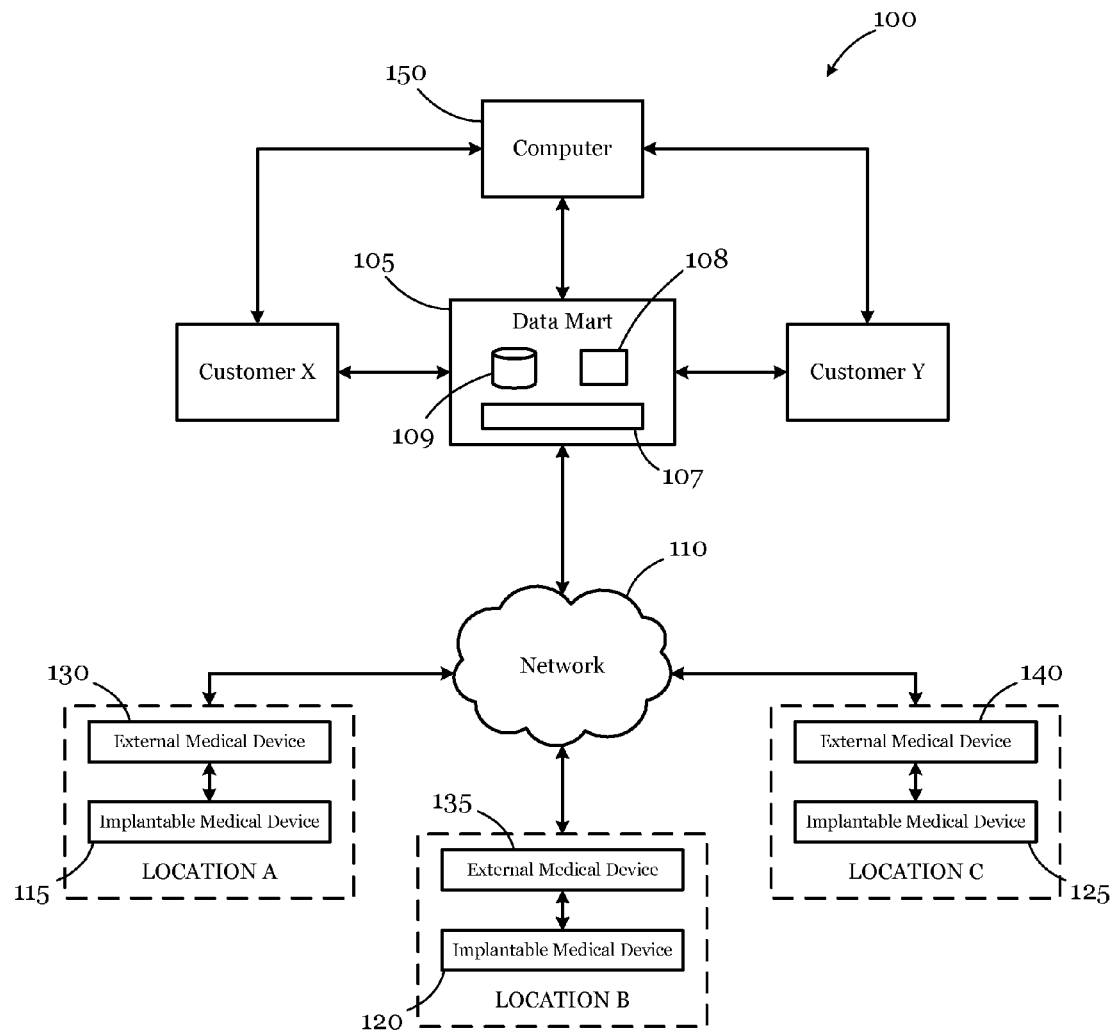
FIG. 1 is a schematic block diagram of an illustrative remote patient management system.

FIG. 1 shows an illustrative remote patient management system 100. The remote patient management system 100 forms part of a system used for remotely managing patients prescribed with medical monitoring or therapy delivery devices. The remote patient management system 100 allows customers to monitor and treat multiple patients located at multiple locations. The illustrative remote patient management system 100 of FIG. 1 shows three locations—Location A, Location B, and Location C. Remote patient management systems are not, however, limited to three locations. Locations A, B, and C can represent, e.g., the residences of three patients. Some embodiments of the remote patient management system 100 allow customers to access data from patients' medical devices without those patients having to visit a clinical facility. The remote patient management system 200 saves valuable time—both for the participating customers and for the patients.

Many different kinds of customers interact with the illustrative remote patient management system 100. Such customers include physicians such as hematologists, electrophysiologists, interventional cardiologists, neurologists, endocrinologists, heart failure specialists, and others. FIG. 1 shows two illustrative customers-Customer X and Customer Y. Remote patient management systems are not, however, limited to two customers. Multiple customers can monitor and treat the same patient. For example, both Customer X and Customer Y can monitor the patients located at Location A, Location B, and/or Location C. Both Customer X and Customer Y can have a computer for communicating electronically with other components of the illustrative remote patient management system 100.

The illustrative remote patient management system 100 includes a data mart 105, which can be located at a central location. The data mart 105 includes a central communication module 107, which allows the data mart 105 to communicate with other components. The central communication module 107 enables the data mart 105 to receive data transmissions from multiple remote medical devices for enabling remote patient management of a population of patients. The central communication module 107 enables the data mart 105 to provide information, such as instructions, to medical devices at multiple locations. The data mart 105 interacts with various types of equipment at each location through a network 110. The network 110 can be a local area network (LAN), a wide area network (WAN), or other suitable telecommunications network, including the Internet. The data mart 105 includes a processor 108 that operates with an associated central database 109. The central database 109 may store patient data and/or programs and algorithms used by the processor in performing patient management operations (e.g., programming and/or interrogating medical devices). The central database 109 can include electronic medical records in a relational database and can include data files and code used for controlling communication with external components.

An implantable medical device ("IMD") 115, 120, 125 (implanted inside of a patient) and an external medical device ("EMD") 130, 135, 140 are located remotely at each of Locations A, B, and C of the illustrative remote patient management system 100. The IMD 115, 120, 125 can be a cardiac stimulation device (e.g., a pacemaker), cardioverter/defibrillator (ICD), a cardiac monitor, a hemodynamic monitor, a neuromuscular stimulator, a drug delivery device, a glucose monitor, or other IMD. The IMD 115, 120, 125 at one location can be the same as or different than the IMD 115, 120, 125 at the other locations. The EMD 130, 135, 140 can be a remote home monitor, programmer, or other EMD. The EMD 130, 135, 140 collects various physiological indicators from IMD patients, such as weight, systemic blood pressure, symptoms, and others. The EMD 130, 135, 140 at one location can be the same or different than the EMD 130, 135, 140 at the other locations. The IMD 115, 120, 125 and/or the EMD 130, 135, 140 can include some or all of the programmable options that are resident in the data mart 105 (e.g., as add-on external algorithms).

The illustrative remote patient management system 100 of FIG. 1 includes a computer 150. In some embodiments, the computer 150 is located in the same location as the data mart 105. In some embodiments, the computer 150 is located remotely from data mart 105. The computer 150 can be a device, or multiple devices working together, that accepts information (in the form of digitalized data) and manipulates it for some result based on a program or sequence of instructions on how the data is to be processed. In some embodiments, the computer 150 may include storage for storing data for some necessary duration.

The data mart 105, the network 110, the IMD 115, 120, 125, the EMD 130, 135, 140, and the computer 150 can be configured to communicate in a variety of ways. In one example, the IMD 115, 120, 125 is configured to communicate with the EMD 130, 135, 140, which is configured to communicate with the data mart 105 via the network 110. In some embodiments, the IMD 115, 120, 125 is configured to communicate with the data mart 105 directly through the network 110. In some embodiments, the data mart 105 communicates directly with either the IMD 115, 120, 125 or the EMD 130, 135, 140 without use of the network 110. Communication between the data mart 105, the network 110, the IMD 115, 120, 125, the EMD 130, 135, 140, and/or the computer 150 can be, for example, bi-directional. The communication configuration can be the same or different with respect to Locations A, B, and C. For example, in some embodiments, the data mart 105 can be configured to communicate with Location B's IMD 120 through the network 110 while being configured to communicate with Location C's IMD 125 through the EMD 140 without the use of the network 110. Each communication among the data mart 105, the network 110, the IMD 115, 120, 125, the EMD 130, 135, 140, and the computer 150 can be initiated by the recipient of the communication ("pull") or by the transmitter ("push").

The content of the information being communicated between the data mart 105, the EMD 130, 135, 140, the IMD 115, 120, 125, and the computer 150 varies according to the particular application. In some applications, the IMD 115, 120, 125 provides data to the data mart 105. The IMD 115, 120, 125 can gather and/or store such data on a continuous or periodic basis. In some embodiments, the IMD 115, 120, 125 communicates some or all of that data to either the EMD 130, 135, 140 or the data mart 105. The EMD 130, 135, 140, for example, communicates some or all of the data received from the IMD 115, 120, 125 to the data mart 105. In some embodiments, the EMD 130, 135, 140 performs one or more processing operations on the data received from the IMD 115, 120, 125.

In some embodiments, the data mart 105 provides information to the IMD 115, 120, 125 and/or to the EMD 130, 135, 140. In one example, Customer X enters instructions related to, e.g., therapy, operating parameters, transfer code, or other instructions, into the data mart 105. The data mart 105 communicates those instructions to the IMD 115, 120, 125 and/or the EMD 130, 135, 140, either through the network 110 or directly. In one example, the patient at Location C requests information related to, e.g., a recently experienced symptom, from the data mart 105. The patient can make the request, e.g., via his/her EMD 125 through the network 110. In response, the data mart 105 can communicate the requested information to the EMD 125 to be displayed to the patient.

In some embodiments, the IMD 115, 120, 125 can gather and/or store information related to parameters such as device performance and various physiological indicators of a patient (e.g., heart rhythm, blood pressure, respiration, patient activity level, heart wall motion, blood chemistry, and the like). In some embodiments, roughly 4000 parameters are provided by the IMD 115, 120, 125 to the data mart 105. Examples of kinds of parameters include pacing parameters, therapy settings, diagnostic data, stored digitized episode data, counter data, and time stamps for various data information, and other relevant parameters.

In some embodiments, all of the information gathered and/or stored in the IMD can be provided to the data mart 105. Such a full transmission of data from the IMD 115, 120, 125 to the data mart 105 can occur on a periodic basis, according to a pre-selected schedule. For example, a full transmission can occur every 90 days. The data mart 105 can index data received from the IMD 115, 120, 125 according to patient, transmission date, IMD serial number, and/or any other factor that would aid in being able to access the data at a later date.

In many cases, the customer can access historical data in remotely caring for patients. For example, the patient at Location C can provide a full transmission related to IMD 125 to the data mart 105 on a transmission date, and the data mart can provide that information to Customer Y. If Customer Y then detected a potentially noteworthy, e.g., blood pressure level in the patient at Location C, Customer Y could retrieve information from the data mart 105 that had been transmitted by the patient at Location C to the data mart 105 at a previous date (e.g., 90 days earlier). Customer Y could then compare the patient's blood pressure on the transmission date with his/her blood pressure on the previous date before determining whether something should be done.

Figure 2:
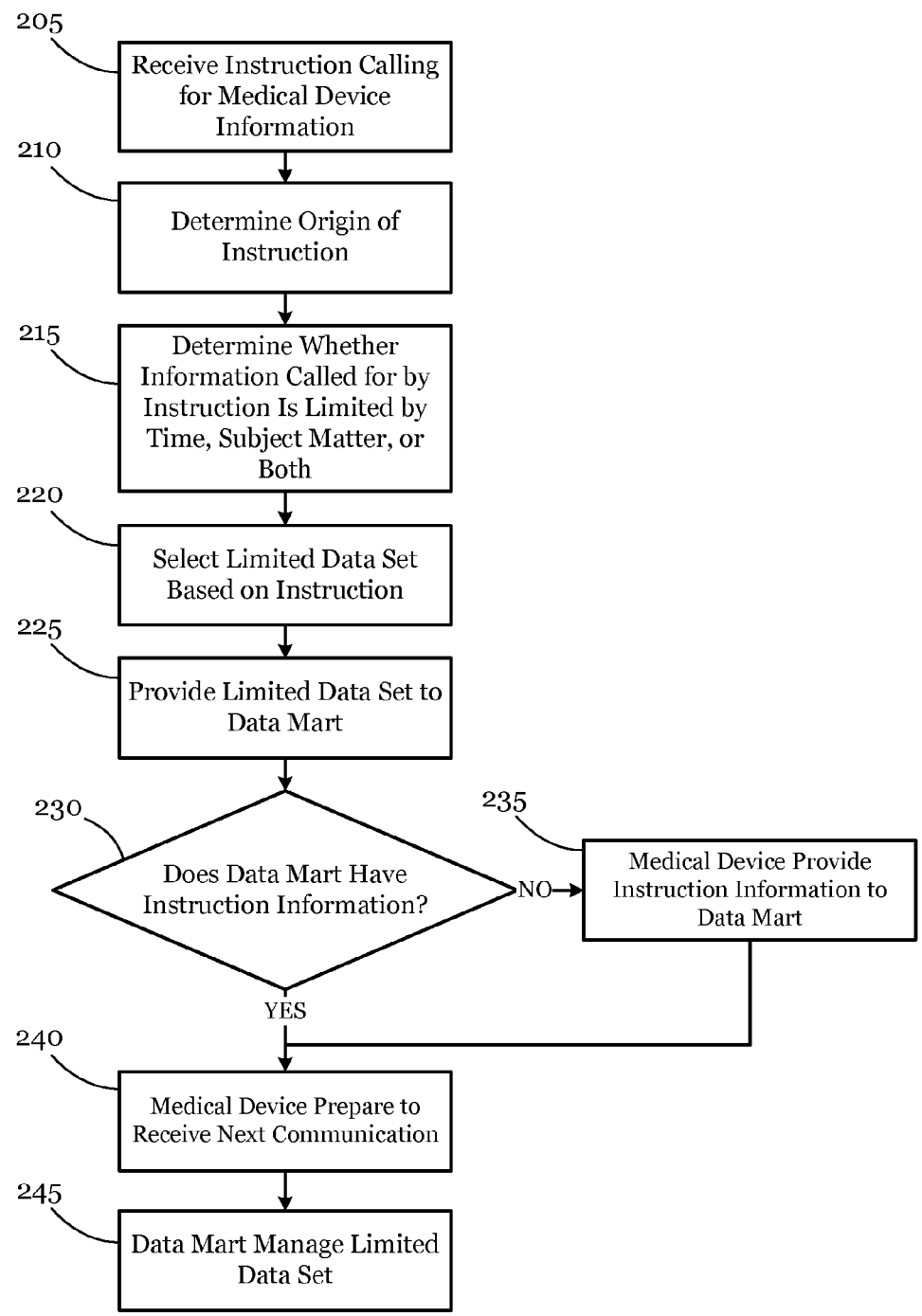
FIG. 2 is a flow chart of a method of remotely caring for a patient having a medical device, the method involving providing less than all information stored in a medical device to a data mart.

In some preferred embodiments, the IMD 115, 120, 125 can provide less than all of the information gathered and/or stored in the IMD 115, 120, 125 to the data mart 105. In some embodiments of the present invention, the IMD 115, 120, 125, the EMD 130, 135, 140, the computer 150, the processor 108 of the data mart 105, and/or a computer at one of the customer sites can have access to a computer-readable medium programmed with instructions for causing a programmable processor to perform one or more methods. FIG. 2 shows an illustrative method of remotely caring for a patient having a medical device. As can be seen, the method can involve providing less than all information stored in a medical device to a data mart. The method of FIG. 2 can provide one or more of the advantages discussed elsewhere herein (e.g., tailoring information to specific requests, preserving IMD batteries, etc.).

In the method of FIG. 2, an instruction calling for medical device information can be received, and the instruction's origin and content can be determined. As shown, an instruction can be received by the medical device calling for medical device information (205). The medical device can receive many kinds of instructions. For example, the medical device can have recently identified and addressed a patient episode (e.g., ventricular tachycardia, ventricular fibrillation, arrhythmia, etc.), and the instruction can call for medical device information related to that patient episode. That medical device information can then be assessed to verify that the medical device is functioning properly.

In another example of an instruction that can be received by the medical device, when a component of the medical device detects that available storage in the medical device has fallen below a threshold level, the instruction can call for information stored since a previous transmission (e.g., all information occurring since the previous transmission, only such information that is related to any patient episode(s), etc.). Absent this feature, when a medical device transmits information on a periodic basis, the medical device storage can fill up before the next scheduled transmission, resulting in overwriting previously stored (and perhaps not yet transmitted) medical device information. Customers often desire all such information for optimum patient care. Additionally, the medical device storage is more likely to fill up during an unexplained "storm" of patient episodes or when a patient transitions from moderate risk to high risk, for example. Often customers are especially interested in medical device information from these periods and are thus especially interested in preventing it from being overwritten. In some embodiments, one or more components of the medical device can detect when a variable is at, or has fallen below or risen above, a predetermined threshold, and can provide an instruction seeking pertinent medical device information.

Another example of an instruction that can be received by the medical device is an instruction relating to a device performance issue. For example, if a component of the medical device determines that a lead has worn to a threshold level or that the medical device's battery has depleted below a threshold level, the component of the medical device can provide an instruction to the medical device calling for medical device information related to the device performance issue. This can assist in verifying and addressing the device performance issue in a timely fashion.

As is mentioned above, in some instances, the instruction can be provided from outside of the medical device, such as by a customer. In some instances, the instruction can be received from a customer and can call for information requested by the customer. In some such instances, the instruction is received according to a regular schedule and calls for information that both (a) has been collected by the medical device since a previous transmission to the customer and (b) is related to care being provided by the customer. This can allow different customers (e.g., electrophysiologists vs. heart failure specialists) to get tailored information at tailored intervals, thereby allowing such customers to focus on the medical device information that is most important to their care of the patient. This can also allow a given customer to pick up a patient's file, realize that he/she would like to review certain medical device information, and retrieve that medical device information with relative ease.

In some instances, the instruction can be received from a patient. As patients get more involved in managing their own care, they may desire to access medical device information. For example, if a patient is experiencing, or has recently experienced, a symptom (e.g., shortness of breath), he or she may want to review medical information. He or she can provide an instruction to the medical device (e.g., through a menu on an EMD) calling for information related to that symptom or information stored within a certain period of time (e.g., the past 24 hours). In this way, patients can access medical device information that was collected by the medical device during a specific time period and/or related to a specific subject matter.

In some instances, the instruction can be provided by a component of the remote patient management system. For example, one or more components of the system can request information from the medical device in order to perform a medical test. In another example, one or more components of the system can request information from the medical device in order to perform a system integrity test.

When the medical device receives an instruction calling for medical device information (205), the medical device can then determine the origin and content of the instruction. In determining the origin of the instruction (210), the medical device can determine whether the instruction is received from a component of the medical device, from a customer, from a component of the remote patient management system, or from a patient (210). As is discussed above, instructions can call for medical device information that was collected by the medical device during a specific time period and/or is related to a specific subject matter. Thus, the medical device can determine whether the information called for by the instruction is limited by time, subject matter, or both (215).

As shown, a limited data set can be selected based on the instruction received (220). The medical device can select the limited data set from medical device information stored in the medical device. In many embodiments, the medical device can search through its large volume of stored information and identify and compile only the medical device information that is responsive to the instruction.

Once selected, the limited data set can be provided to the data mart (225) (e.g., directly or indirectly through a network). In most cases, the data mart manages the limited data set based on the corresponding instruction. The data mart can determine whether it has information related to the instruction (230). If it does, the medical device can simply prepare to receive the next communication (240) (e.g., a new instruction, one or more of the communications from the data mart discussed below, etc.). If the data mart does not have instruction information, the medical device can provide such instruction information to the data mart (235) and then prepare to receive the next communication (240). With the limited data set and the instruction information at the data mart, the limited data set can be managed (245).

The limited data set and the corresponding instruction information can come in a variety of forms. For example, the limited data set can include medical device information related to a particular patient episode, and the instruction information can be a request to the data mart to determine whether the patient episode was correctly identified. In another example, the limited data set can include medical device information stored since a previous transmission to the data mart, and the instruction information can be an explanation that the available storage in the medical device has fallen below a threshold level, along with a request to store the limited data set with the patient's file. In another example, the limited data set can include medical device information related to a device performance issue, and the instruction information can be a request asking the data mart to investigate the device performance issue further. In another example, the limited data set can include the medical device information requested by a customer or patient, and the instruction information can be a request asking the data mart to create a report explaining what the data is. Several other examples are possible.

Figure 3A:
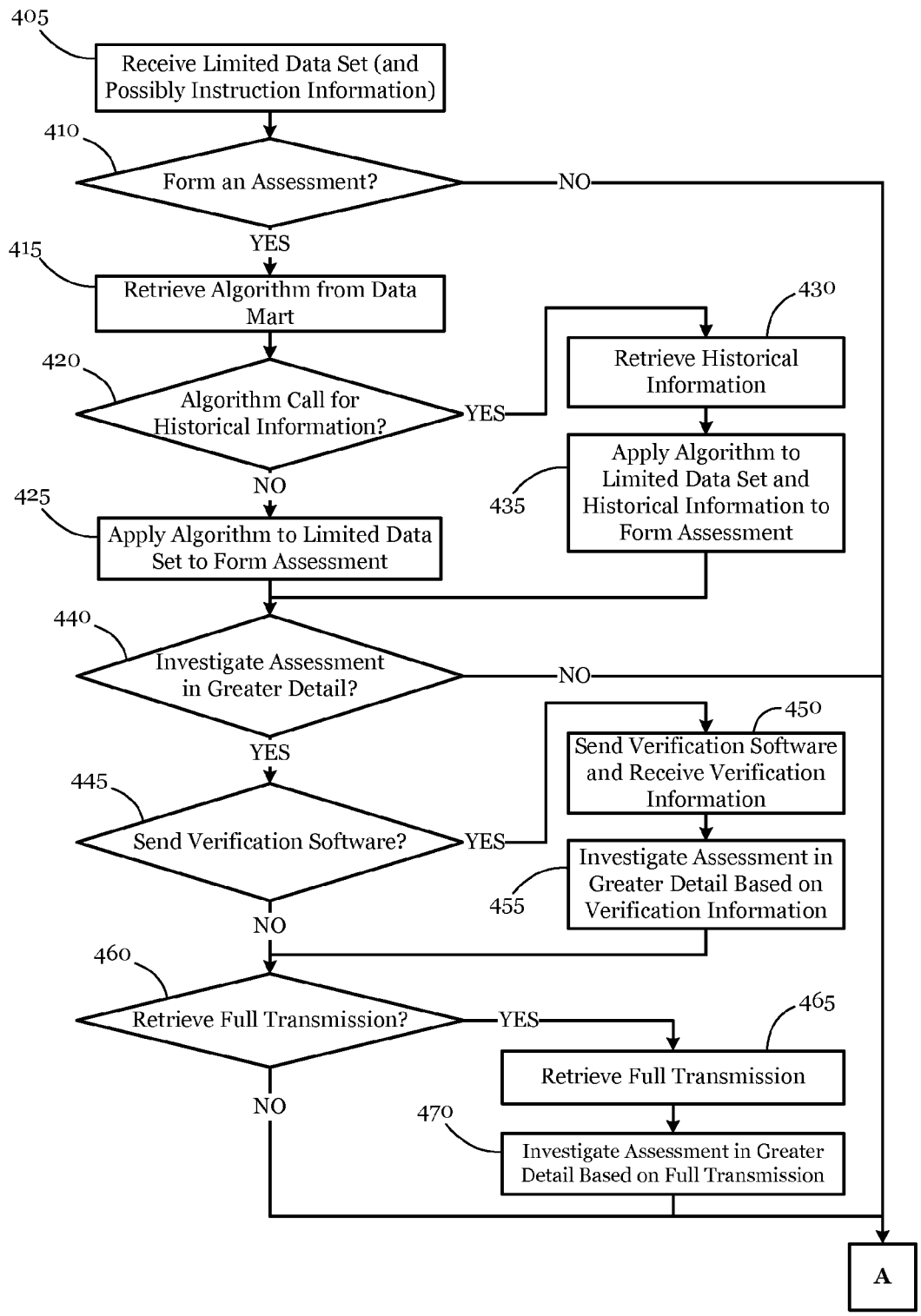
FIGS. 3A-3B are a more detailed flow chart of an illustrative method of remotely caring for a patient having a medical device, the method involving managing a limited data set at a data mart.
Figure 3B:
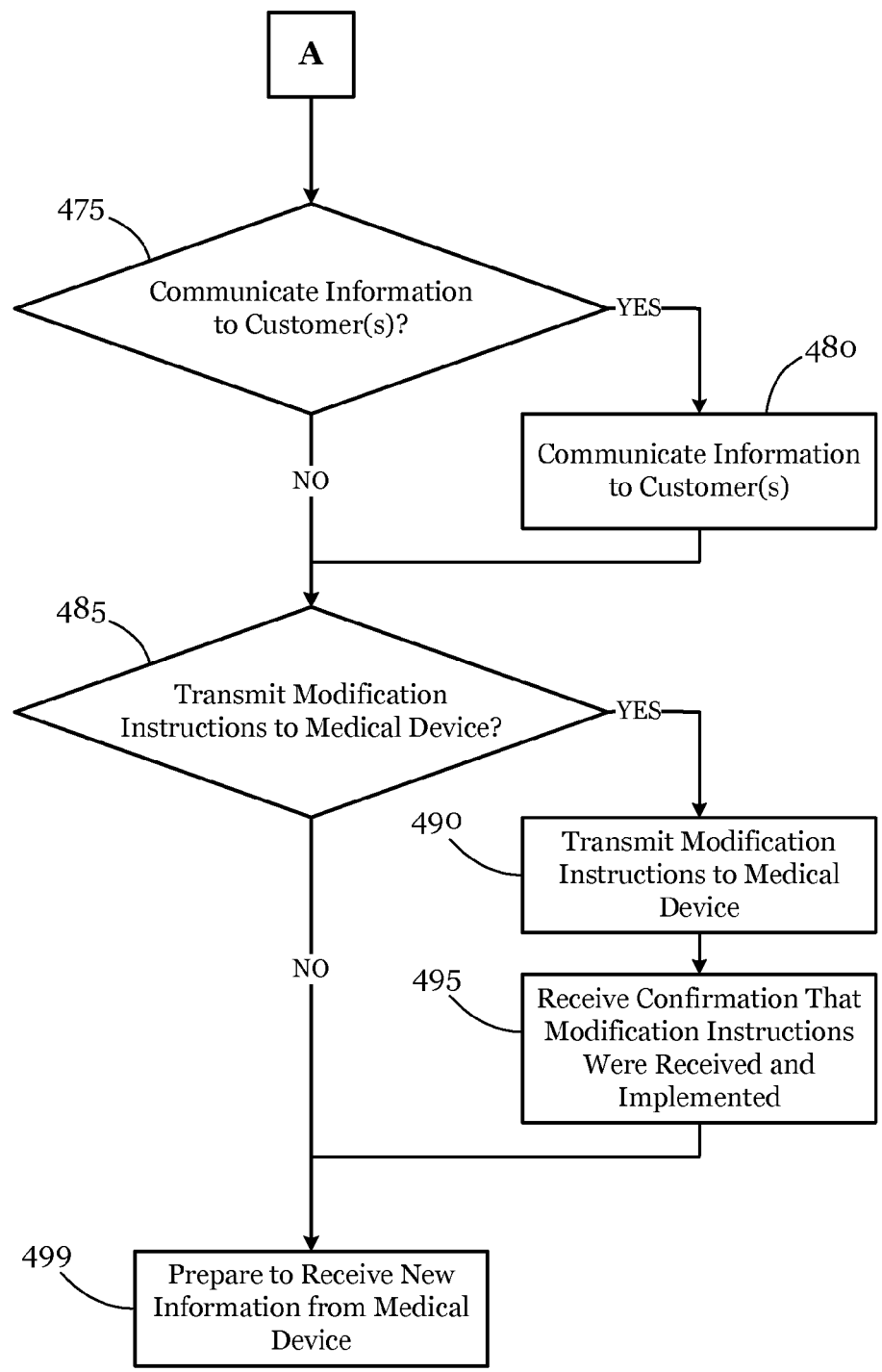

FIGS. 3A-3B provide illustrations for some of the ways in which the limited data set can be managed at the data mart according to the instruction information. As mentioned above, and as shown in FIG. 3A, the data mart can receive the limited data set, with or without instruction information (405). Some embodiments involve forming an assessment of the limited data set (410) (e.g., at the data mart or at a separate computer). In such embodiments, an algorithm can be retrieved from the data mart (415). For example, in embodiments in which the data mart is asked to verify that the medical device properly identified a patient episode, the data mart can retrieve an algorithm for determining whether the patient indeed experienced that patient episode based on the limited data set. The same would hold true for embodiments in which the data mart is asked to monitor device performance. Forming an assessment of a limited data set, as opposed to a full transmission, poses significantly less stress to the data mart. If no assessment is to be formed, the data mart can proceed to the method illustrated in FIG. 3B.

Referring again to FIG. 3A, in some embodiments, the algorithm calls for historical information related to the patient and/or the medical device in addition to the limited data set (420). As is discussed above, the data mart can store large volumes of information from a wide variety of patients. In some cases, the data mart may be able to provide an improved assessment of the limited data set by taking into account such historical information as previously gathered medical device information from the patient, information related to other patients who have similar characteristics or similar medical devices, and so on. Taking historical information into account can identify the presence or absence of one or more trends, which can provide significant benefit to customers in their care for the patients. Accordingly, in many embodiments, historical information can be retrieved from the data mart (430), and the algorithm can be applied to the limited data set and the historical information to form an assessment (435). If the algorithm does not call for historical information, the algorithm can be applied to the limited data set to form an assessment (425).

In some cases in which the data mart forms an assessment of the limited data set, the sensitivity of various sensors in the medical device can be increased, resulting in more frequent assessments by the data mart. The medical device can make a very preliminary determination of a device or patient condition, and the data mart can perform the analysis to funnel down to a more detailed assessment. While this may result in a significant number of occasions in which the medical device's preliminary determination is incorrect, it substantially reduces the likelihood of an actual device or patient condition going untreated. Moreover, because most of the analysis is being performed at the data mart rather than the medical device, the impact on the medical device's battery is minimal. In cases such as these, the customer can be notified (e.g., remotely) and/or the patient can be notified (e.g., through alert tones) if there is an actual patient or device condition, and he/she can be undisturbed if there is not.

For example, in some cases, a medical device is configured to monitor three criteria as being indicative of lead failure. In such cases, the medical device commonly provides a full transmission to the data mart when the medical device determines that two of the three lead failure criteria are present. With systems as described above, however, this functionality can be enhanced. The medical device can provide medical device information related to those three criteria to the data mart when the medical device determines that even one of the three criteria are present. The data mart can then perform a more thorough analysis to determine whether there are any lead failure issues. Thus, the medical device can provide smaller amounts of more focused medical device information to the data mart on a more frequent basis with less strain on the medical device battery.

Once an assessment of the limited data set is made, some embodiments provide that the assessment can be investigated in greater detail (440). For example, the instruction can ask the data mart to assess whether a particular condition merits further investigation. If the data mart determines that the condition does indeed merit further investigation, the data mart can proceed with that investigation. If the assessment is not investigated in greater detail, the data mart can proceed to the method illustrated in FIG. 3B.

Referring again to FIG. 3A, the further investigation can take a variety of forms. In some embodiments, the investigation can involve sending verification software to the medical device (445), and verification information can be received at the data mart based on the verification software (450). In many embodiments, the verification software can perform a clinical test on a patient. For example, a customer can determine, based on the medical device information he/she has reviewed, that a patient may have sleep apnea. The customer can then prescribe a sleep apnea test to verify his/her initial determination. The software to run the test can be downloaded to the patient's device, and the results can then be uploaded back to the data mart and reported to the customer. Such an investigation often comes into play in the context of a possible device performance issue. The assessment can then be investigated in greater detail based on the verification information (455).

In many embodiments, further investigation of the limited data set can involve retrieving a full transmission from the medical device (460). In some such embodiments, a full transmission can be retrieved from the medical device (465), and the assessment can then be investigated in greater detail based on the full transmission (470). Having the data mart form an assessment based on the limited data set before initiating a full transmission can significantly reduce the number of full transmissions, thereby leading to several of the advantages discussed elsewhere herein.

In several embodiments, further investigation of the limited data set can involve both sending verification software and retrieving a full transmission. For example, the data mart can initiate sending verification software or retrieving a full transmission first and then, depending on the information received, initiate the other second. In another example, the timing of the verification software and the full transmission can overlap.

In some embodiments, information can be communicated to one or more customers (475). In such embodiments, the data mart communicates information to the customer(s) (480). In some such embodiments, the information communicated to the customer(s) is based on an assessment made (and, in some cases, investigated in greater detail). In some such embodiments, the information includes some or all of the limited data set. In some such embodiments, some or all of the limited data set is transmitted from the data mart to a customer without performing any analysis on the limited data set. In the event that only a portion of the limited data set is transmitted to the customer, that portion can be selected according to a specific request by a customer or according to a pre-selected program.

In some embodiments, information can be communicated to one or more patients. As is discussed elsewhere herein, a patient can request certain medical device information. When the medical device has provided that information to the data mart, the data mart can provide it to the patient. In some embodiments, the data mart can provide an alert (e.g., triggering an audible signal) to the patient through the medical device (either an IMD or an EMD or both).

In some embodiments, modification instructions can be transmitted to the medical device (485). In such embodiments, the data mart transmits modification instructions to the medical device (490). In many such embodiments, the modification instructions call for modification of (i) how the medical device monitors for and/or treats conditions, (ii) how the medical device stores medical device information, and/or (iii) the time intervals at which the medical device transmits medical device information to the data mart. At the end of the process illustrated in FIGS. 3A-3B, the data mart can prepare to receive new information from a medical device (499).

In the foregoing detailed description, the invention has been described with reference to specific embodiments. However, it may be appreciated that various modifications and changes can be made without departing from the scope of the invention as set forth in the appended claims. Thus, some of the features of preferred embodiments described herein are not necessarily included in preferred embodiments of the invention which are intended for alternative uses.

What is claimed is:

1. A method of remotely caring for a patient having a medical device, the method comprising:
   providing, by a processor, an instruction to a medical device, the instruction calling for medical device information that the instruction limits by at least one of: being collected by the medical device during a specific time period; or being related to a specific subject matter;
   selecting a limited data set consisting of only medical device information that is responsive to the instruction, from medical device information stored in the medical device, the limited data set comprising at least one of: information collected during the specific time period or information related to the specific subject matter as called for by the instruction;
   transmitting the limited data set from the medical device to a data mart;
   determining whether the data mart has access to instruction information that indicates how the instruction limits the medical device information selected and transmitted by the medical device;
   providing the instruction information from the medical device to the data mart in response to the data mart determining it does not have access to the instruction information; and
   managing the limited data set at the data mart according to the instruction information, wherein managing the limited data set at the data mart includes analyzing the limited data set based on historical information stored at the data mart.

2. The method of claim 1, wherein the instruction is provided to the medical device by a component of the medical device.

3. The method of claim 1, wherein the instruction is provided to the medical device from outside of the medical device.

4. The method of claim 1, wherein managing the limited data set includes (i) retrieving an algorithm from the data mart, (ii) applying the algorithm to the limited data set to form an assessment of the limited data set, (iii) retrieving a full transmission of all data stored on the medical device from the medical device, and (iv) investigating the assessment in greater detail based on the full transmission.

5. The method of claim 1, wherein managing the limited data set includes (i) retrieving an algorithm from the data mart, (ii) applying the algorithm to the limited data set to form an assessment of the limited data set, (iii) sending verification software to the medical device, the verification software being configured to perform an additional test based on the analysis of the limited data set, (iv) receiving verification information at the data mart based on the verification software, and (v) investigating the assessment in greater detail based on the verification information.

6. The method of claim 1, wherein managing the limited data set includes (i) retrieving an algorithm from the data mart, (ii) applying the algorithm to the limited data set to form an assessment of the limited data set, the method further comprising communicating information to a customer based on the assessment.

7. The method of claim 1, wherein managing the limited data set includes (i) retrieving an algorithm from the data mart, (ii) retrieving historical information related to the patient and/or the medical device from the data mart, and (iii) applying the algorithm to the limited data set and the historical information.

8. The method of claim 1, wherein managing the limited data set includes transmitting modification instructions to the medical device, the modification instructions calling for modification of (i) how the medical device monitors for and/or treats conditions, (ii) how the medical device stores medical device information, and/or (iii) time intervals at which the medical device transmits medical device information to the data mart.

9. A non-transitory computer-readable storage medium comprising instructions for causing one or more programmable processors to:
   provide, by a processor, an instruction calling for medical device information that the instruction limits by at least one of: being collected by a medical device during a specific time period; or being related to a specific subject matter;

receive a limited data set consisting of only medical device information that is responsive to the instruction, from medical device information stored in the medical device, the limited data set comprising at least one of: information collected during the specific time period or information related to the specific subject matter as called for by the instruction;

determine whether the data mart has access to instruction information that indicates how the instruction limits the medical device information selected and transmitted by the medical device;

retrieve the instruction information from the medical device in response to determining that the data mart does not have access to the instruction information; and manage the limited data set according to the instruction information based on historical information stored at the data mart.

10. The computer-readable storage medium of claim 9, wherein the instruction (i) is provided in response to a patient episode, (ii) calls for information related to the patient episode, and (iii) asks the data mart to determine whether the patient episode was correctly identified.

11. The computer-readable storage medium of claim 9, wherein the instruction (i) is provided in response to a detected device performance issue, (ii) calls for information related to the device performance issue, and (iii) asks the data mart to investigate the device performance issue further.

12. The computer-readable storage medium of claim 9, wherein the instruction (i) is provided by a customer and (ii) calls for information requested by the customer.

13. The computer-readable storage medium of claim 12, wherein the instruction further (iii) is provided according to a regular schedule and (iv) calls for information that both (a) has been collected by the medical device since a previous transmission to the customer and (b) is related to care being provided by the customer.

14. The computer-readable storage medium of claim 9, wherein the instruction (i) is provided from a patient and (ii) calls for information related to a symptom he/she is experiencing or has recently experienced.

15. A method of remotely caring for a patient having a medical device, the method comprising:

receiving a limited data set at a data mart from a medical device, the limited data set having been selected based on an instruction calling for medical device information stored in the medical device and consisting of only medical device information that is responsive to the instruction, that the instruction limited by at least one of: being collected by the medical device during a specific time period; or being related to a specific subject matter;

determining whether the data mart has access to instruction information that indicates how the instruction limits the medical device information selected and transmitted by the medical device;

retrieving the instruction information from the medical device in response to the data mart determining that it does not have access to the instruction information; and managing the limited data set at the data mart according to the instruction information, wherein managing the limited data set at the data mart includes analyzing the limited data set based on historical information stored at the data mart.

16. The method of claim 15, wherein managing the limited data set includes providing at least part of the limited data set to a separate computer for analysis.

17. The method of claim 15, wherein managing the limited data set includes (i) retrieving an algorithm from the data mart, (ii) applying the algorithm to the limited data set to form an assessment of the limited data set.

18. The method of claim 15, wherein managing the limited data set includes (i) retrieving an algorithm from the data mart, (ii) retrieving historical information related to the patient and/or the medical device from the data mart, and (iii) applying the algorithm to the limited data set and the historical information.

19. The method of claim 1, wherein managing the limited data set comprises evaluating at the data mart whether a condition merits further investigation, and in response to determining that a condition merits further investigation, transmitting an instruction to the medical device calling for the medical device to increase the sensitivity of data received from a sensor of the medical device.

20. The method of claim 5, wherein the verification software is configured to perform at least one of a clinical test on the patient to verify the assessment of the limited data set or a test to investigate a possible device performance issue.

21. The method of claim 1, wherein the historical information comprises information related to other patients with similar characteristics or similar medical devices, and wherein analyzing the limited data set based on the historical information stored at the data mart comprises comparing the limited data set with the information related to other patients with similar characteristics or similar medical devices.

22. The method of claim 1, further comprising providing the instruction to the medical device when remaining data storage on the medical device falls below a threshold.

23. The method of claim 1, further comprising providing the instruction to the medical device when a variable detected by the medical device reaches a threshold.

24. The method of claim 1, further comprising providing the instruction to the medical device when a lead connected to the medical device has worn to a threshold level.

25. The method of claim 1, further comprising providing the instruction to the medical device when a battery on the medical device has depleted below a threshold.

26. A method of providing for remote care of a patient with a medical device, the method comprising:

receiving, by a processor of a medical device, an instruction calling for medical device information that the instruction limits by at least one of: being collected by the medical device during a specific time period; or being related to a specific subject matter;

selecting a limited data set consisting of only medical device information that is responsive to the instruction, from medical device information stored in the medical device, the limited data set comprising at least one of: information collected during the specific time period or information related to the specific subject matter as called for by the instruction;

transmitting the limited data set from the medical device to a data mart;

receiving, by the processor of a a medical device, a request for instruction information that indicates how the instruction limits the medical device information selected and transmitted by the medical device; and providing the instruction information from the medical device to the data mart in response to the data mart determining it does not have access to the instruction information.

27. The method of claim 26, wherein a component of the medical device provides the instruction to the medical device when remaining data storage on the medical device falls below a threshold.

28. The method of claim 26, wherein a component of the medical device provides the instruction to the medical device when a variable detected by the medical device reaches a threshold.

29. The method of claim 26, wherein a component of the medical device provides the instruction to the medical device when a lead connected to the medical device has worn to a threshold level.

30. The method of claim 26, wherein a component of the medical device provides the instruction to the medical device when a battery on the medical device has depleted below a threshold.

* * * * *

UNITED STATES PATENT AND TRADEMARK OFFICE
CERTIFICATE OF CORRECTION

| | | |
|---|---|---|
| PATENT NO. | : 8,290,791 B2 | Page 1 of 1 |
| APPLICATION NO. | : 12/181429 | |
| DATED | : October 16, 2012 | |
| INVENTOR(S) | : Amisha S. Patel et al. | |

It is certified that error appears in the above-identified patent and that said Letters Patent is hereby corrected as shown below:

Col. 12, line 56, delete "...of a a medical device..." and insert in place thereof -- of a medical device --

Signed and Sealed this
Fourth Day of December, 2012

David J. Kappos
*Director of the United States Patent and Trademark Office*